(12) United States Patent
MacAulay et al.

(10) Patent No.: US 6,794,658 B2
(45) Date of Patent: Sep. 21, 2004

(54) LIGHT MODULATED MICROARRAY READER AND METHODS RELATING THERETO

(75) Inventors: Calum E. MacAulay, Vancouver (CA); Pierre M. Lane, Vancouver (CA)

(73) Assignee: Digital Optical Imaging Corporation, Bellingham, WA (US)

( * ) Notice: Subject to any disclaimer, the term of this patent is extended or adjusted under 35 U.S.C. 154(b) by 37 days.

(21) Appl. No.: 10/165,168

(22) Filed: Jun. 6, 2002

(65) Prior Publication Data

US 2003/0002040 A1 Jan. 2, 2003

Related U.S. Application Data

(60) Provisional application No. 60/296,635, filed on Jun. 6, 2001.

(51) Int. Cl.[7] ................................................ G01N 21/64
(52) U.S. Cl. ................................. 250/458.1; 250/459.1; 250/461.1
(58) Field of Search ........................... 250/458.1, 459.1, 250/461.1

(56) References Cited

U.S. PATENT DOCUMENTS 6,583,424 B2 * 6/2003 Staton et al. ............. 250/461.2

FOREIGN PATENT DOCUMENTS

| DE | 199 40 752 | 4/2000 | ............. G03F/7/00 |
| DE | 199 14 279 | 9/2000 | ........... G01N/21/17 |

OTHER PUBLICATIONS

International Search Report, PCT/US02/17899, Dec. 23, 2002.

* cited by examiner

Primary Examiner—Constantine Hannaher
Assistant Examiner—Timothy J. Moran
(74) Attorney, Agent, or Firm—Graybeal Jackson Haley LLP

(57) ABSTRACT

Microarray readers and methods that compensate for target spots that are too dim or too bright for the microarray reader to accurately measure. The readers adjust the amount of light directed at or received from specific non-acceptable target spots, such that dim spots receive more excitation light and overly bright spots receive less. This increases or decreases, respectively, their measured brightness, which in turn effectively increases the range over which a microarray reader can accurately measure the spots, and can also improve the signal-to-noise ratio and other aspects of the measurements.

64 Claims, 7 Drawing Sheets

- Uniform max 63242
- Modulated max 62976
- Uniform spot area 1290 SD 155
- Modulated spot area 1314 SD 143
- Uniform background 380 SD 159
- Modulated background 409 SD 99
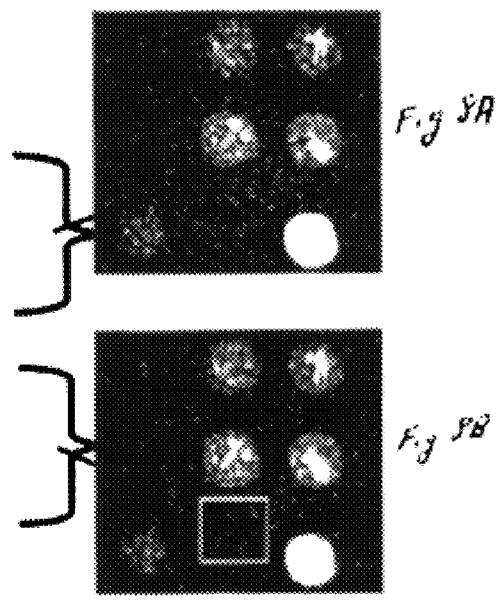
Fig 8A
Fig 8B
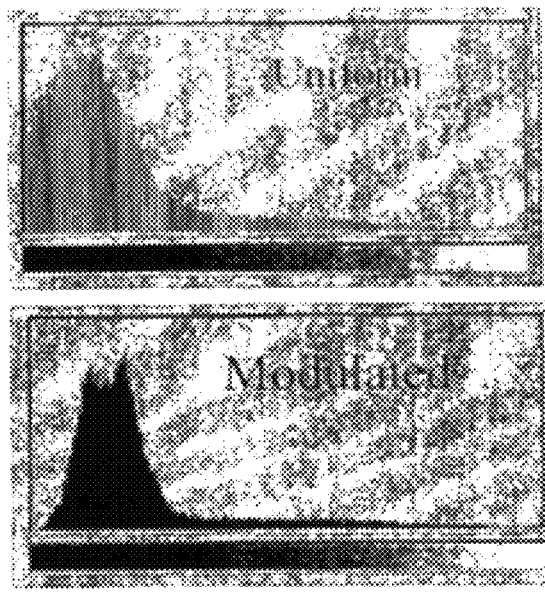
Fig 9A
Fig 9B

LIGHT MODULATED MICROARRAY READER AND METHODS RELATING THERETO

CROSS-REFERENCE TO RELATED APPLICATIONS

The present application claims priority from U.S. provisional patent application No. 60/296,635, filed Jun. 6, 2001.

BACKGROUND

"Microarrays" are devices used in biotechnology and other science research, and can be made by putting a large number of tiny droplets of DNA (or other target such as cDNA or proteins) on a glass slide. Short pieces of DNA, called probes, are then applied to the DNAs on the slide. Typically, the probes are fluorescent, so they light up when short wavelength light is shone on them (the probes can also be labeled with other substances to reflect or otherwise emanate light when they are scanned). Microarrays can be used, for example, to study how large numbers of genes interact with each other (genes are made of DNA), or how a cell is able to simultaneously control vast numbers of genes.

The probes stick to the microarray wherever the probes find target stretches of DNA called complementary DNA strands. The microarrays are then put into a scanning microarray reader that measures the brightness of each fluorescent dot: the brighter the dot, the more probe (and thus the more target DNA or other biological material) is present. This can indicate, for example, how active the target is, or where it is on the slide.

Microarrays can be used, for example, to study genomic content, how large numbers of genes interact with each other (genes are made of DNA), or how a cell is able to simultaneously control vast numbers of genes (expression patterns). Different types of microarrays include, but are not limited to, cDNA arrays, oligonucleotide arrays and protein arrays.

Some general concepts about microarrays, and the microarray readers that measure the dots, are discussed in more scientific terms in the following paragraphs.

Fluorescence based microarray readers suffer from limited dynamic range with respect to the possible intensities of target spots in, for example, cDNA expression microarrays. Systems which use scanning spots and photomultiplier tubes (PMTs) for detection are reported to possibly have a $\sim 10^6$ dynamic range but may have a $10^4$ to $10^5$ dynamic range in practice. Most charge couple device (CCD) imaging microarray readers have about a $\sim 10^3$ dynamic range (12 bit-digitization, 4096 levels, 40,000-1,000,000 electron well depths, 200:1 up to 1000:1 possible signal-to-noise ratio).

The intensity of a fluorescent target spot on a microarray is a function of factors such as how long the target spot is sampled (data sampling time, which can be dwell time for scanning spot systems and integration time for CCD imaging systems), the intensity of the illumination (illumination intensity), the sensitivity of the detector (quantum efficiency, signal transducer, or measurement sensitivity), and the accuracy of digitization (pulse counting or voltage digitization). Coordination and control of these factors is difficult, so measuring spot intensity over a wide range is difficult.

Accordingly, there has gone unmet a need for improved methods of precisely measuring the brightness of the target spots on a microarray over a wide range of target spot intensity. The present invention provides this and other advantages.

SUMMARY

Target spots on a microarray that are too dim or too bright for the microarray reader to accurately measure are a problem, for example because they fall outside of certain threshold levels so the microarray reader cannot accurately measure them, or because target spots that are too bright can also hinder the measurement of neighboring target spots due to glare or other interference. Typically, the intensity of light emanating from target spots is proportional to the amount of light shown or incident on the target spots; the more light that is incident on the target spot (excitation or illumination light), the brighter the light coming from the target spot. The present invention takes advantage of this and adjusts the amount of light directed at specific non-acceptable target spots (for example, those spots which fall outside the dynamic range of the system in use), such that dim spots receive more excitation light and overly bright spots receive less.

Similarly, in conjunction with or instead of such actions, the present invention adjusts the amount of light received from specific non-acceptable target spots, such that the detector receives more light from dim spots and less light from overly bright spots. This increases or decreases, respectively, their measured brightness, which in turn effectively increases the range over which a microarray reader can accurately measure the spots, and can also improve the signal-to-noise ratio and other aspects of the measurements. In some embodiments, the present invention can increase the range of the microarray reader by up to about 1000 times or more, and improve the signal-to-noise ratio for target spots up to about 16 times or more.

In one aspect, the present invention provides automated methods of reading a microarray comprising, a) providing an initial representation of a microarray comprising a plurality of target spots illuminated by illumination light having a designated intensity; b) determining from the initial representation whether at least one of the target spots has an emanating light intensity that can be not between selected upper and lower threshold values, and designating such target spot a non-acceptable target spot; and, c) modulating the designated intensity of the illumination light via an automated upstream selective light modulator located in an illumination light path substantially at a conjugate image plane of the sample to provide a modulated illumination light and an adjusted target spot that emanates an adjusted light intensity between the selected upper and lower threshold values.

In some embodiments, the methods further comprise measuring the amount of modulation of the designated intensity of the illumination light and measuring the adjusted light intensity, then correlating the amount of modulation with the adjusted light intensity to provide a measure of the actual signal strength of the target spot. In this and other embodiments of the invention (unless expressly stated otherwise or clear from the context), all embodiments, aspects, features, etc., of the present invention can be mixed and matched, combined and permuted in any desired manner. The methods can further comprise determining an amount of a probe located at the adjusted target spot from the measure of the actual signal strength of the target spot. The methods are suitable for detecting any light emanating spot, such as reflective, fluorescent or other light.

The methods can be implemented according to various formulae. Such formulae include:

$$SS(x,y)=K*CCDS(x,y)/II(x,y) \qquad (1)$$

where,
SS(x,y) can be the actual signal strength of the target spot,
K can be a constant for the system,
(CCDS(x,y)) can be the adjusted light intensity, and
(II(x,y)) can be the modulated illumination light.

$$SS(x,y)=K*PB(II(x,y),\text{fluoro})*CCDS(x,y)/II(x,y) \qquad (2)$$

where,
SS(x,y) can be the actual signal strength of the target spot,
K can be a constant for the system,
PB(II(x,y),fluoro) can be a photobleaching function based on illumination energy/intensity and a fluorophore being excited,
(CCDS(x,y)) can be the adjusted light intensity, and
(II(x,y)) can be the modulated illumination light.

$$SS(x,y)=K*PB(II(x,y),\text{fluoro},x,y)*CCDS(x,y)/II(x,y) \qquad (3)$$

where,
SS(x,y) can be the actual signal strength of the target spot,
K can be a constant for the system,
PB(II(x,y),fluoro,x,y) can be a photobleaching function based on illumination energy/intensity, a fluorophore being excited, and a spatial variation term,
(CCDS(x,y)) can be the adjusted light intensity, and
(II(x,y)) can be the modulated illumination light.

The modulated illumination light can be modulated by changing its illumination intensity, by changing its duration of illuminating the target spot, or otherwise as desired. The initial representation can comprise a precompiled map of expected data for the target spots of the microarray, or an initial image of the plurality of target spots illuminated by the illumination light having the designated intensity, typically taken by a same microarray reader that implements other elements of the methods. The initial image can be taken substantially immediately before the determining, modulating, measuring and correlating are implemented.

The methods can further comprise repeating any desired element, such as the determining, modulating, measuring and correlating in an iterative fashion, for example using the measure of the actual signal strength as the initial representation. The probe can be selected such that the modulation is linearly related to the adjusted light intensity.

In certain embodiments, the methods can be implemented using a microarray reader comprising the upstream selective light modulator, and a light detector disposed downstream from the microarray in a detection light path substantially at a conjugate image plane of the sample, wherein the selective light modulator and the light detector can be operably connected to at least one controller containing computer-implemented programming that controls transmissive characteristics of the upstream selective light modulator and that compiles the modulated illumination light and the adjusted light intensity, and wherein the controller spatially varies the transmissive characteristics of the selective light modulator to vary the modulated illumination light impinging on the non-acceptable target spots of the microarray such that light emanating from the non-acceptable target spots can be between the threshold levels. The upstream selective light modulator can comprise a digital micromirror device and the detector can comprise a charge coupled device.

In other aspects, the present invention provides automated methods of reading a microarray comprising, a) providing an initial representation of a microarray comprising a plurality of target spots illuminated by illumination light having a designated intensity; b) determining from the initial representation whether at least one of the target spots has an emanating light intensity that can be not between selected upper and lower threshold values, and designating at least one of such target spots a non-acceptable target spot; and, c) modulating the emanating light intensity via an automated downstream selective light modulator located in a detection light path substantially at a conjugate image plane of the sample to provide a modulated detection light comprising an adjusted emanating light intensity that can be between the selected upper and lower threshold values.

The methods can further comprise measuring the amount of modulation of the detection light and measuring the modulated detection light, then correlating the amount of modulation with the modulated detection light to provide a measure of the actual signal strength of the target spot. The methods can also further comprise determining an amount of a probe located at the non-acceptable target spot from the measure of the actual signal strength of the target spot.

Such methods can be implemented using a microarray reader comprising the selective light modulator, and a light detector disposed in a detection light path substantially at a conjugate image plane of the sample and downstream from the microarray and the downstream selective light modulator, wherein the selective light modulator and the light detector can be operably connected to at least one controller containing computer-implemented programming that controls transmissive characteristics of the downstream selective light modulator and that compiles the modulated detection light and the adjusted light intensity, and wherein the controller selectively varies the transmissive characteristics of the selective light modulator to vary the modulated detection light impinging on the non-acceptable target spots of the microarray such that light received at the detector can be between the threshold levels.

In a further aspect, the present invention provides microarray reader comprising an automated upstream selective light modulator located upstream of a microarray in an illumination light path substantially at a conjugate image plane of the sample, and a light detector disposed downstream from the microarray in a detection light path substantially at a conjugate image plane of the sample, wherein the selective light modulator and the light detector can be operably connected to at least one controller containing computer-implemented programming that controls transmissive characteristics of the upstream selective light modulator and that compiles an amount of modulated illumination light when the upstream selective light modulator can be modulated and an adjusted light intensity emanating from a target spot on a microarray receiving the modulated illumination light, and wherein the controller selectively varies the transmissive characteristics of the selective light modulator to vary the modulated illumination light impinging on at least one non-acceptable target spot of the microarray such that light emanating from the at least one non-acceptable target spot can be between selected threshold levels.

The controller can further comprise computer-implemented programming that implements other aspects of the methods discussed herein. For example, the programming can control measuring the amount of modulation of the illumination light and control measuring the adjusted light intensity, then correlate the amount of modulation with the adjusted light intensity to provide a measure of the actual signal strength of the target spot. The programming can determine an amount of a probe located at the at least one non-acceptable target spot from the measure of the actual signal strength of the target spot.

In another aspect, the present invention provides microarray reader comprising an automated downstream selective light modulator located downstream of a microarray in a detection light path substantially at a conjugate image plane of the sample, and a light detector disposed in the detection light path substantially at a conjugate image plane of the sample and downstream from the downstream selective light modulator and the microarray, wherein the downstream selective light modulator and the light detector can be operably connected to at least one controller containing computer-implemented programming that controls transmissive characteristics of the downstream selective light modulator and that compiles an amount of modulated detection light when the downstream selective light modulator can be modulated and an adjusted light intensity received by the detector, and wherein the controller selectively varies the transmissive characteristics of the downstream selective light modulator to vary the modulated detection light emanating from at least one non-acceptable target spot of the microarray such that light received at the detector from the at least one non-acceptable target spot can be between selected threshold levels.

As above, the controller can further comprise programming that implements other features of the methods. The controller can control measuring the amount of modulation of the detection light and control measuring the adjusted light intensity, then correlate the amount of modulation with the adjusted light intensity to provide a measure of the actual signal strength of the target spot. The controller can also determine an amount of a probe located at the at least one non-acceptable target spot from the measure of the actual signal strength of the target spot.

In still other aspects, the present invention includes automated methods of reading a microarray comprising, a) providing an initial representation of a microarray comprising a plurality of target spots illuminated by illumination light having a designated intensity; b) determining from the initial representation whether at least one of the target spots has an emanating light intensity that can be not between selected upper and lower threshold values, and designating at least one of such target spots as a non-acceptable target spot; c) selectively illuminating the non-acceptable target spot via selectively transmitting light to the microarray using a first automated upstream selective light modulator located in an illumination light path substantially at a conjugate image plane of the sample; and, d) modulating the designated intensity of the illumination light via a second automated upstream selective light modulator located in the illumination light path substantially at a conjugate image plane of an aperture diaphragm of the objective lens, to provide a modulated illumination light and an adjusted target spot that emanates an adjusted light intensity between the selected upper and lower threshold values.

The methods can also modulate the designated intensity of the illumination light via the first automated upstream selective light modulator located in the illumination light path substantially at the conjugate image plane of the sample, and can determine an amount of a probe located at the adjusted target spot.

In yet further aspects, the present invention comprises automated methods of reading a microarray comprising, a) providing an initial representation of a microarray comprising a plurality of target spots illuminated by illumination light having a designated intensity; b) determining from the initial representation whether at least one of the target spots has an emanating light intensity that can be not between selected upper and lower threshold values, and designating at least one of such target spots as a non-acceptable target spot; c) selectively detecting light from the non-acceptable target spot via selectively transmitting light from the microarray using a first automated downstream selective light modulator located in a detection light path substantially at a conjugate image plane of the sample; and, d) modulating the emanating light intensity via a second automated downstream selective light modulator located in a detection light path substantially at a conjugate image plane of an aperture diaphragm of the objective lens, to provide a modulated detection light comprising an adjusted emanating light intensity between the selected upper and lower threshold values.

The methods can further comprise also modulating the emanating light intensity of the detection light via the first automated downstream selective light modulator located in the detection light path substantially at the conjugate image plane of the sample.

In additional aspects, the present invention includes microarray readers configured to implement such methods. For example, the readers can comprise a first automated upstream selective light modulator located upstream of a microarray in an illumination light path substantially at a conjugate image plane of the sample, a second automated upstream selective light modulator located upstream of the microarray in the illumination light path substantially at a conjugate image plane of an aperture diaphragm of the objective lens, and a light detector disposed downstream from the microarray in a detection light path substantially at a conjugate image plane of the sample, wherein the first and second selective light modulators and the light detector are operably connected to a suitable controller.

Alternatively, the microarray reader can comprise a first automated downstream selective light modulator located downstream of a microarray in a detection light path substantially at a conjugate image plane of the sample, a second automated downstream selective light modulator located downstream of the microarray in the illumination light path substantially at a conjugate image plane of an aperture diaphragm of the objective lens, and a light detector disposed in the detection light path substantially at a conjugate image plane of the sample and downstream from the first and second downstream selective light modulators and the microarray, wherein the first and second selective light modulators and the light detector are operably connected to a suitable controller.

These and other aspects, features and embodiments of the invention are set forth within this application, including the following Detailed Description and attached drawings. In addition, various references are set forth herein, including in the Cross-Reference To Related Applications, that discuss in more detail certain systems, apparatus, methods and other information; all such references are incorporated herein by reference in their entirety and for all their teachings and disclosures, regardless of where the references may appear in this application.

BRIEF DESCRIPTION OF THE DRAWINGS

FIGS. 8A and 8B depict photographs of microarrays read with and without modulation, respectively.

FIGS. 9A and 9B presents histograms of the measurement data from FIGS. 8A and 8B.

DETAILED DESCRIPTION

Figures 1A, 1B:
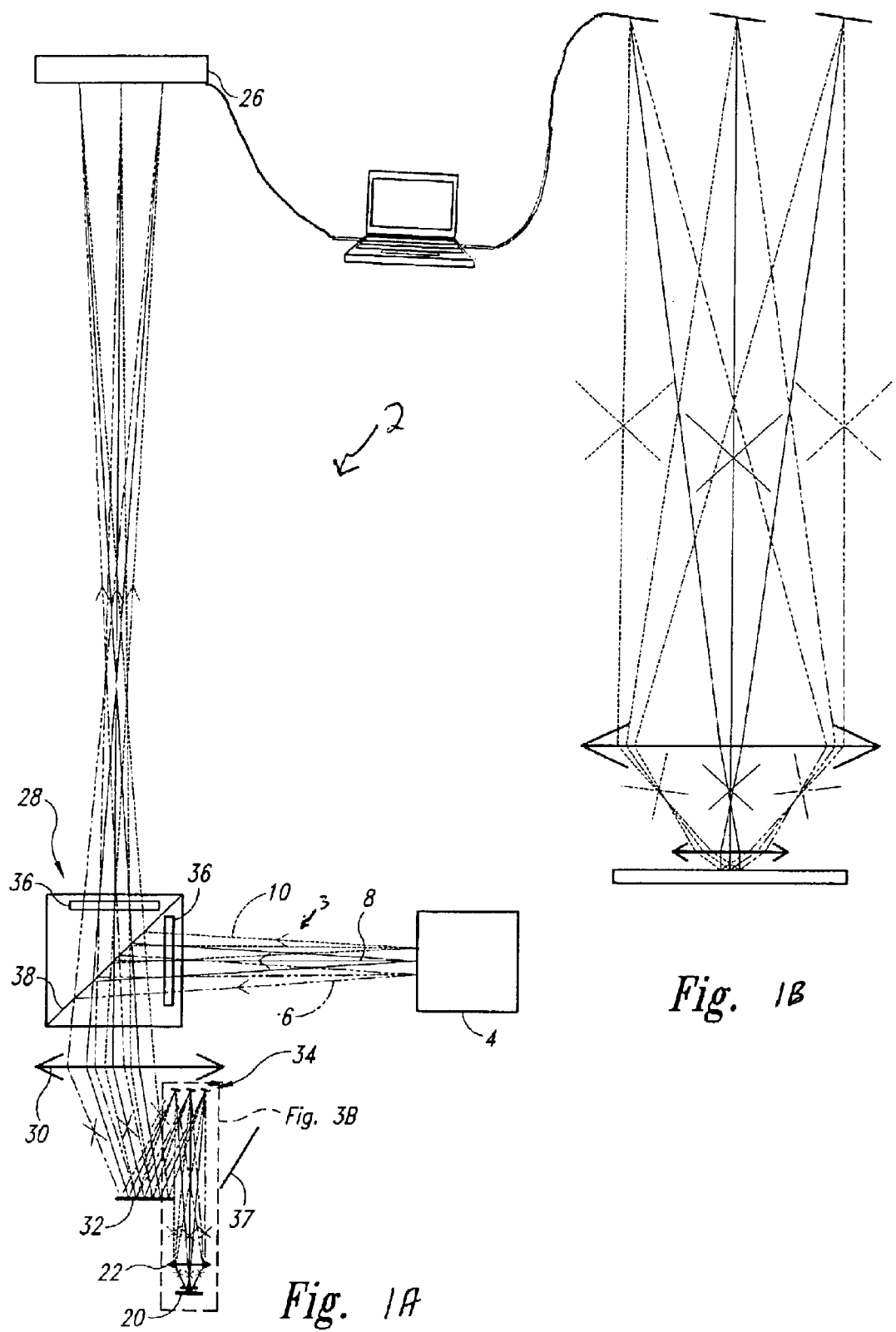
FIGS. 1A and 1B provide a schematic view and an expanded schematic view of a microarray reader according to one embodiment of the present invention that comprises a selective light modulator to replace the field diaphragm.

The present invention enhances the dynamic range over which microarray readers can measure target spots on a microarray, and can improve the signal-to-noise ratio of such readers, by dynamically modifying the illumination properties of the readers. Modulating the amount of light directed at specific target spots, such that dimmer target spots receive more excitation light and overly bright target spots receive less light, increases or decreases their measured brightness to more desirable ranges better suited for the detector, and in some cases less likely to interfere with readings of adjacent target spots. The dynamically modified illumination properties can, if desired, be used instead of, or in conjunction with, modifications to data sampling time, detector sensitivity, and digitization accuracy (pulse counting or voltage digitization). In some embodiments, the dynamically modified illumination properties can increase the range of the microarray reader by up to about 1000 times, and improve the signal-to-noise ratio for target spots up to about 16 times.

Before discussing the Figures, it will be helpful to review some definitions and to discuss various methods related to the microarray readers of the present invention.

Definitions

A "selective light modulator" (SLM) is a device that is able to selectively modulate light. In the present invention, selective light modulators are disposed in the light path of a microarray reader. The selective light modulator can be pixelated and comprise an array of individual light transmission pixels, which is also known as a spatial light modulator, which are a plurality of spots that have transmissive characteristics such that they either transmit or pass the light along the light path or block the light and prevent it from continuing along the light path (for example, by absorbing the light or by reflecting it out of the light path). Such pixelated arrays are known, having also been referred to as a multiple pattern aperture array, and can be formed, for example, by an array of twisted-nematic or ferroelectric liquid crystal devices, by a digital micromirror device (DMD), or by electrostatic microshutters. See, U.S. Pat. No. 5,587,832; R. Vuelleumier, Novel Electromechanical Microshutter Display Device, Proc. Eurodisplay '84, Display Research Conference September 1984. Digital micromirror devices can be obtained from Texas Instruments, Inc., Dallas, Tex., U.S.A. Other suitable devices include microoptoelectromechanical system (MOEMs) with suitably high contrast abilities (for example, 200-to-1 or 1000-to-1 contrast ratios) between on-and-off states.

The "illumination light path" is the light path from a light source to a microarray, while a "detection light path" is the light path for light emanating from a microarray to a detector. Light emanating from a microarray includes light that reflects from a microarray, is transmitted through a microarray, or is created within the microarray, for example, fluorescent light that is created within a microarray pursuant to excitation with an appropriate wavelength of light.

A "conjugate image plane of the sample" is a plane in either the illumination light path or the detection light path wherein an image of the microarray is recreated; and thus is a conjugate image plane of the microarray. The light detector (s) is typically located in one such site in the detection light path. The conjugate image planes of the sample define locations that can control the size and location of spots on the microarray that are illuminated and/or detected (depending upon whether the conjugate plane is in the illumination light path or the detection light path). The image plane of the sample is the plane wherein the microarray is located, although the image plane of the sample can be greater or smaller than the size of the actual microarray, for example if either a plurality of light paths are provided or if the illumination area is greater or smaller than the size of the microarray.

A "conjugate image plane of an aperture diaphragm of the objective lens" is a plane in either the illumination or detection light path where an image of the aperture diaphragm of the objective lens is recreated. Typically, this image plane also contains a recreation of the image of the light source, which in the present invention can be any light source such as a white light, an arc lamp or a laser. The conjugate image planes of the aperture diaphragm of the objective lens define locations that control the angle of illumination light that is ultimately impinged on a microarray, as well as the angle of detection light that emanates from a microarray (the "angle of illumination" and "angle of detection" refer to the angle of the light that is either impinging upon or emanating from a microarray).

A "controller" is a device that is capable of controlling a selective light modulator, a detector or other elements of the apparatus and methods of the present invention. For example, the controller can control the light communication characteristics of a selective light modulator, control the on/off status of pixels of a pixelated selective light modulator or light detector (such as a charge coupled device (CCD) or charge injection device (CID)), and/or compile data from the selective light modulator or the detector, including using such data to make or reconstruct images of a microarray or as feedback to control an upstream selective light modulator. Typically, a controller is a computer or other device comprising a central processing unit (CPU) or other logic-implementation device, for example a stand alone computer such as a desk top or laptop computer, a computer with peripherals, a local or internet network, etc. Controllers are well known in the art and selection of a desirable controller for a particular aspect of the present invention is within the scope of the art in view of the present disclosure.

"Upstream" and "downstream" are used in their traditional sense wherein upstream indicates that a given device is closer to a light source, while downstream indicates that a given object is farther away from a light source.

The scope of the present invention includes both means plus function and step plus function concepts. However, the terms set forth in this application are not to be interpreted in the claims as indicating a "means plus function" relationship unless the word "means" is specifically recited in a claim, and are to be interpreted in the claims as indicating a "means plus function" relationship where the word "means" is specifically recited in a claim. Similarly, the terms set forth in this application are not to be interpreted in method or process claims as indicating a "step plus function" relationship unless the word "step" is specifically recited in the claims, and are to be interpreted in the claims as indicating a "step plus function" relationship where the word "step" is specifically recited in a claim.

Other terms and phrases in this application are defined in accordance with the above definitions, and in other portions of this application.

Turning to some methods of the present invention, the methods comprise dynamically modifying the illumination properties of the reader. In certain embodiments, this is effected by illuminating a microarray to provide an initial representation of the microarray, which can be an image, precompiled map of expected data (for example from previous experiments or as intentionally designed), or other representation of the photonic or light intensity emanating from the microarray. Such initial representation of desired spots on the microarray is measured, and then for any spot falling outside of desired parameters, i.e., non-acceptable target spots have greater than or less than certain upper and lower threshold levels (maxima and minima) of emanating light, respectively, increasing or decreasing the amount of illumination light directed to such non-acceptable target spot by selectively modulating the light via a spatial light modulator (SLM). The amount of modulation is then correlated with the amount of light detected by the detector; the intensity of the illumination light and the emanating light intensity from the given target spot on the microarray are considered together. The system then provides a reading of the actual light intensity emanating from the target spot, taking into account both the intensity of the illumination light and the intensity of the detected light. Because the dynamic range of the spatial light modulator and the detector are additive (or multiplicative, depending upon the method of representation), the system has a substantially increased dynamic range compared to systems that do not modulate the illumination light. The following paragraphs typically discuss the methods and systems for exemplary purposes using a digital micromirror device(s) as the SLM(s) and CCD(s) as the detector(s), but other structures are also suitable.

In some embodiments of effecting such methods, before readings are taken (or while readings are being taken, as desired) specific mirrors of the DMD or other SLM are correlated with specific pixels or areas of the CCD detector or other pixelated detector. This can be done using any desired, appropriate calibration technique, for example techniques similar to those used to map DMD mirrors (or the light controllers of other SLMs, such as MOEMs) to fiber cores discussed in U.S. patent application Ser. No. 09/738, 257, entitled Methods And Apparatus For Imaging Using A Light Guide Bundle And A Spatial light modulator, filed Dec. 14, 2000. Once mapping has been done for a particular set up, typically it does not need to be repeated until either the DMD or CCD is moved relative to the other.

In some embodiments, the DMD is located at or near a conjugate image plane of the sample in either an epi-illumination or transmission microarray reader configuration; other configurations are also possible. For each new microarray area or target spot that is imaged, an initial image is acquired using a pre-set exposure time. The bright areas and the dim areas (spots) in the image are then noted. Next, the DMD mirrors corresponding to the very bright target spots are set to illuminate less intensely, and the DMD mirrors corresponding to the dim target spots are set to illuminate more intensely, etc. A second image is then obtained, which image has more uniform target spot image intensities. The actual amount of target material (e.g., labeled probe) located within a target spot can be determined by the emanating light intensity of the target spot in the image and by the intensity (e.g., dwell time) of the illumination directed to each target spot.

The dynamic range of the DMD-CCD system is that of the DMD plus that of the CCD. Thus, if the DMD can provide 1000 different illumination levels and the CCD has 1000 distinct grey levels of detection, then (ignoring photon noise and other possible artifacts) the system has a dynamic range (within a single microarray) of 1,000,000 or $10^6$, a 1,000 fold increase.

It is also possible to use the combination of the DMD and CCD dynamic ranges to provide superior signal-to-noise characteristics. Briefly, the number of photons detected (counted) at lower grey level values can have a worse signal-to-noise ratio because of photostatistics or other hindering influences. For example, if a maximum grey level of 10,000 corresponds to a full well capacity of 10,000 electrons, then signals with a value of 10,000 have a noise level of 100 (signal-to-noise of 100-to-1) whereas signals with a grey level value of 100 have a noise value of 10 (signal-to-noise of 10-to-1). So target spots (in a cDNA microarray, for example) that are about 100 times different in their emanating light intensity (the strong signal spots having a signal level of 10,000 and the weak spots having a signal level of 100) vary significantly in their signal-to-noise ratios (by about 10 fold in this example).

In accordance with the present invention, the illumination light intensity on the target spots can be modulated such that the grey levels of each target spot at the detector are about 10,000 by illuminating the weak signal spot with 100 times more intense light than the strong signal spot. This results in the two target spots having closer, up to substantially the same, signal-to-noise values or ratios. The overall signal strength of each target spot is provided by the intensity (or duration) of the illumination signal in combination with the detected light, so an enhanced, and more consistent signal-to-noise ratio can be achieved simultaneously with improved dynamic range.

The methods and system can be set up such that for each frame or image of a microarray to be measured (target spots read) either a priori information about target spot strength and location from a database or an initial image of the frame can be used to modulate the intensity of the illumination light to get uniformly high grey level intensity images for each target spot. From the individual spot illumination intensity or duration, the strength of each spot can be calculated. In addition, the results can be further improved by either measuring the photobleaching characteristics of each target spot or fluorophore by using a sequence of images or by using previously acquired photobleaching characteristic information to correct the measured spot strength.

Ignoring photobleaching, the relationship between the target spot strength (i.e., emanating light intensity of the target spot; SS(x,y)), illumination intensity or duration (II(x,y)), and detected CCD signal (CCDS(x,y)) can be represented as:

$$SS(x,y)=K*CCDS(x,y)/II(x,y)$$

where K is a constant for the system.

Including a photobleaching function, PB(II(x,y),fluoro), which is a function of illumination energy/intensity and the fluorophore being excited, the relationship becomes:

$$SS(x,y)=K*PB(II(x,y),\text{fluoro})*CCDS(x,y)/II(x,y)$$

Since, in some circumstances, the photobleaching process can be a function of other factors (oxygen, chemical environment, etc.) which may vary from location to location within the microarray, PB(II(x,y), fluoro) can, if desired, be determined on the fly and incorporate an addition spatial variation term PB(II(x,y),fluoro,x,y). To determine the photobleaching behavior on a location-by-location basis, a sequence of images (two or more) can be taken, and the spatial photobleaching function can be determined for the specific microarray frame. Various forms of photobleaching functions can be used (single exponential, double exponential, multi exponential, etc.), and the multiple image data used to generate the model parameters which give the suitable fit to the observed data. This spatially dependent photobleaching function can then be used to determine the signal strength in the microarray.

$$SS(x,y)=K*PB(II(x,y),\text{fluoro},x,y)*CCDS(x,y)/II(x,y)$$

In addition to the above mentioned benefits, the equations can improve measurement of target spot strength by accounting for differential photobleaching of different fluorophores.

The more uniform target spot intensities described above and elsewhere herein simplify glare or scatter corrections, if any, for the measured image, and can correct, for example, for the nonlinear or other undesired behavior of the imaging optics. An image which has had glare and scatter removed from the image data produces more accurate spot intensity measures, for example because the spots are more accurate and because the background values used to determine spot intensity values are more representative of what actually occurred in the microarray.

The Figures

Exemplary microscopic systems suitable for use with the present invention are depicted in FIGS. 1–5B. The systems can be confocal, wide field, or otherwise configured as desired. Other systems can also be used.

FIGS. 1A and 1B depict a schematic drawing of a microarray reader 2 comprising a selective light modulator in an upstream conjugate image plane of the sample. Microarray reader 2 comprises a light source 4 that emits a plurality of illumination light rays, such as excitation light rays, along illumination light path 3 toward the microarray 20. The light rays have been divided into first light rays 6, second light rays 8 and third light rays 10. The light rays first pass through a filter 36, then reflect off a dichroic mirror 38 (the dichroic mirror 38 and filter 36 are maintained in a dichroic mirror and filter block set 28) and through a projection lens 30, followed by reflection off a simple mirror 32 onto a selective light modulator, which in the figure is a digital micromirror device 34. As depicted in the figure, all of the individual light transmission pixels (i.e., micromirrors in the figure) are on, and thus all of light rays 6, 8, 10 are transmitted to objective lens set 22 and microarray 20. If one or more of the individual light transmission pixels were turned off, the light rays would be directed to a second or third location, for example a beam stop or additional detector 37. The light is then reflected or fluoresced off microarray 20 and back through objective lens 22, off digital micromirror device 34 and simple mirror 32 and then transmitted through projection lens 30. The light then continues past dichroic mirror 38, filter 36 and ultimately to light detector 26. The light is transmitted from the microarray to the light detector 26 along detection light path 5.

In FIGS. 1A and 1B, digital micromirror device 34 is placed in a conjugate image plane of the sample in each of the illumination light path 3 and the detection light path 5. Light detector 26 can be any desired light detector, for example, a detector comprising a charged coupled device (CCD), a charged injection device (CID), a complementary metal-oxide semi-conductor (CMOS), or a video camera. If desired, it is possible to use a plurality of different light detectors either in series or in an adjacent relationship or in any other desired relationship. In some typical embodiments, the light detector is a CCD or a CID or other light detector that comprises as array of individual detection pixels, which indicates a plurality of spots, typically on the same order of the same size as the pixels in the selective light modulator.

In some embodiments, the detection array of individual detection pixels in light detector 26 corresponds to and is aligned with the illumination array of individual light transmission pixels in the selective light modulator. Accordingly, the detection array can have an equivalent number of pixels, each of which is aligned with the pixels of the selective light modulator array, or groups of such pixels are aligned with each other. In certain embodiments, this alignment can be effected by using a single digital micromirror device at a desired conjugate image plane in both the illumination light path and the detection light path, for example as depicted in FIGS. 1A and 1B.

FIGS. 1A and 1B depict an epi-fluorescence microarray reader, which means that the light is incident on the microarray from above, but it could also represent a transmission microarray reader, which would mean the light would be incident from below and transmit through the microarray, if a separate second selective light modulator were used in the detection light path (or if appropriate mirrors or other devices were to direct the detection light path back to a single digital micromirror device).

Figure 2:
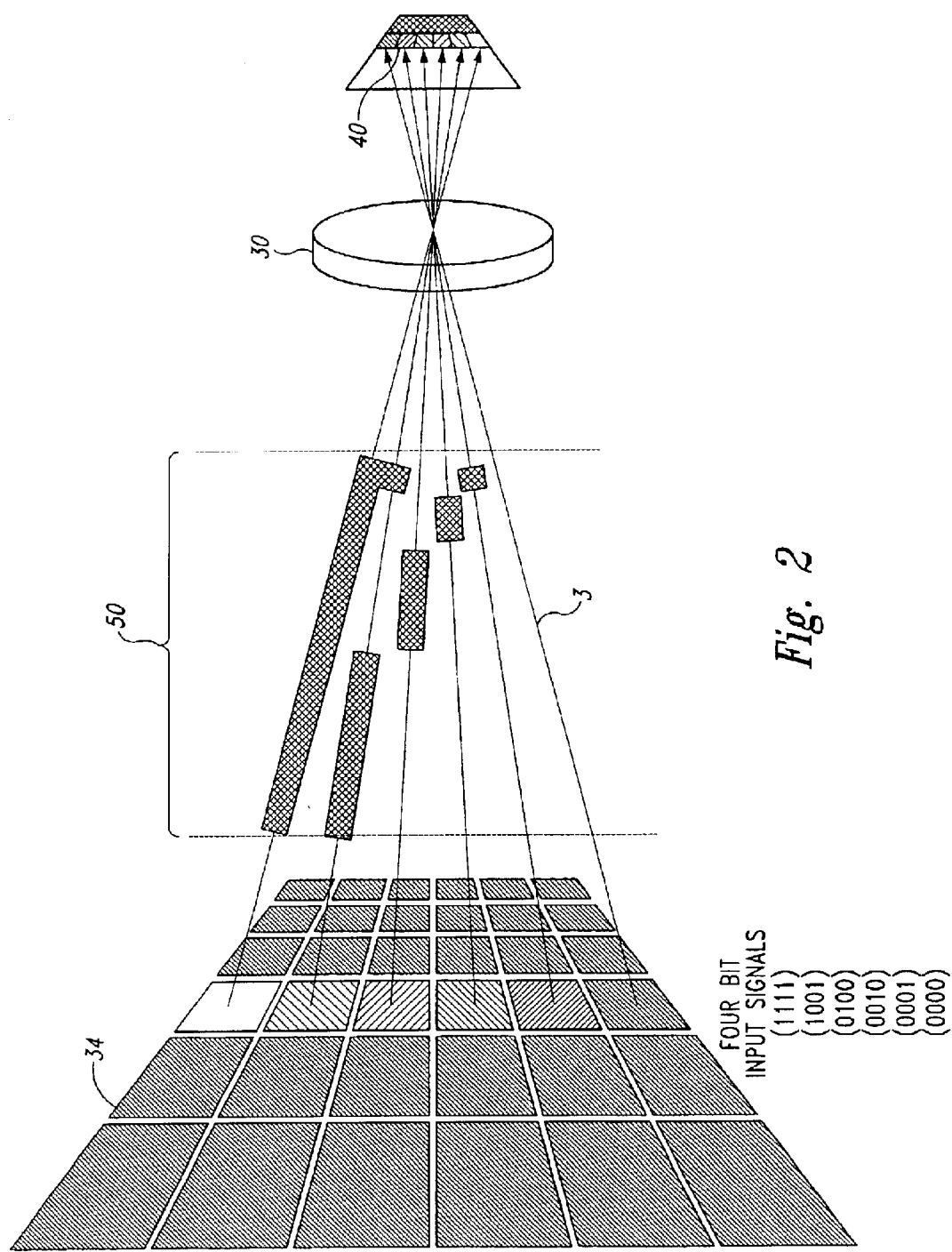
FIG. 2 provides a schematic view of a digital micromirror device transmitting light as different functions of time.

FIG. 2 depicts a schematic representation of a microarray reader comprising a selective light modulator in a conjugate image plane of the sample, and illustrates how a digital micromirror device can produce grey-scale intensities. In particular, digital micromirror device 34 reflects a plurality of light beams along illumination path 3 to projection lens 30 and into image plane 40. In a central column of the digital micromirror device 34, each of the digital micromirrors has a different percentage of time in which the mirror is on instead of off. For example, the top most micromirror in the figure is on 100% of the time, while the bottom most micromirror in the column in the figure is off 100% of the time, while the four mirrors between the two have an on/off status that is between 100% on and 100% off. Thus, each of the light rays from the central column have a different video field time 50, which video field time corresponds to the amount of on and off time for the particular micromirror.

Figure 3A:
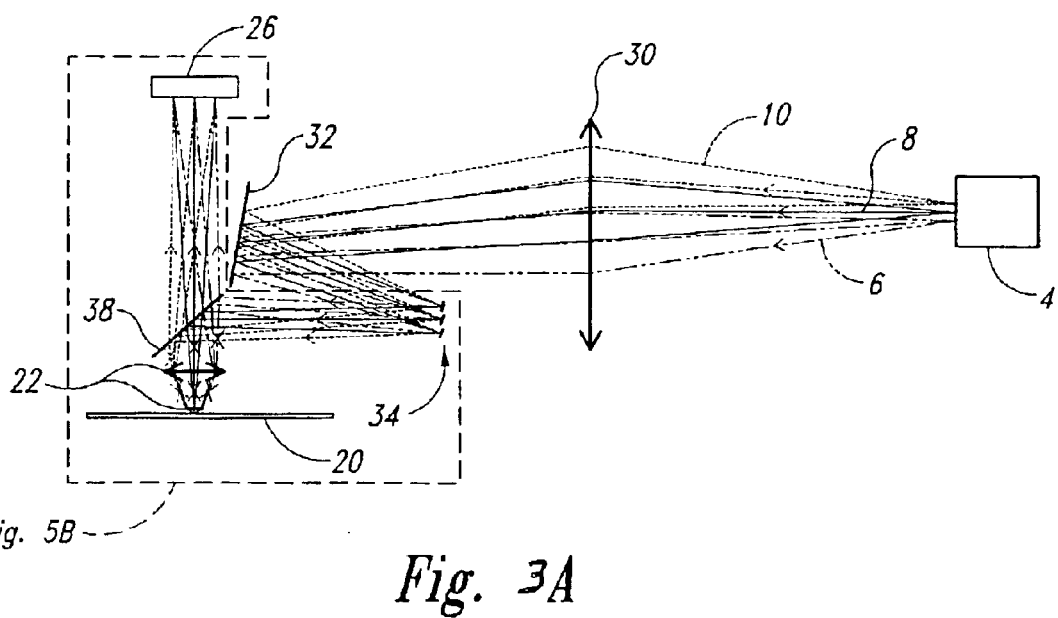
FIGS. 3A and 3B provide a schematic view and an expanded schematic view of a further embodiment of a microarray reader according to the present invention in which an selective light modulator is positioned upstream of, or before, a dichroic mirror.
Figure 3B:
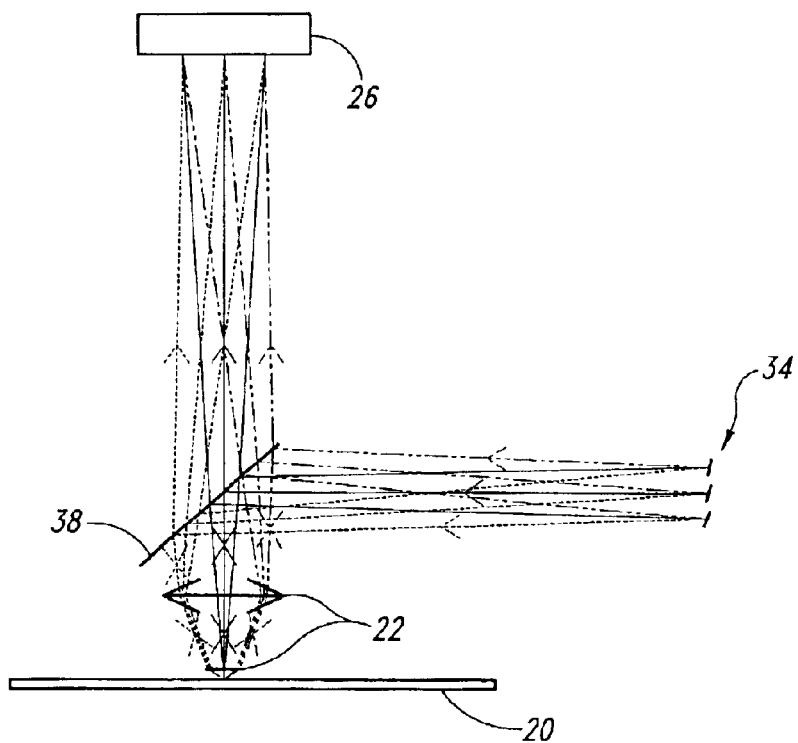

FIGS. 3A and 3B depict a schematic view of a microarray reader that is similar to the microarray reader set forth in FIGS. 1A and 1B, except that the selective light modulator 34 is disposed solely in the illumination light path and not in the illumination light path 3.

Figure 7A:
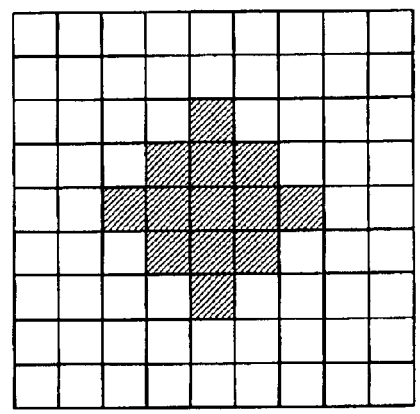
FIG. 7A provides a schematic view of a selective light modulator in which multiple adjacent pixels are switched "on" to define an illumination spot of a desired size.
Figure 7B:
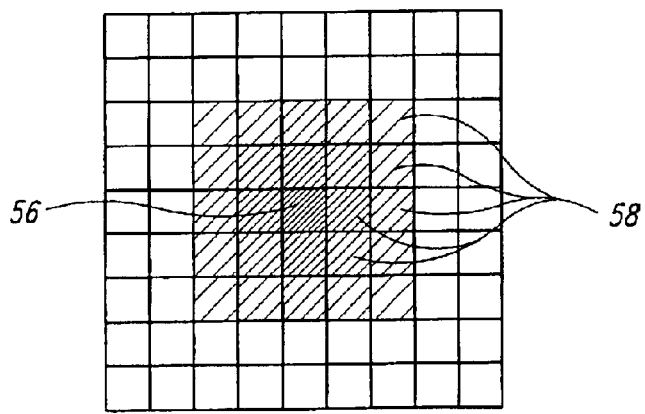
FIG. 7B provides a schematic view of an selective light modulator in which multiple adjacent pixels are rapidly switched on and off such that when time averaged the mirrors are partially on or partially off to define a Gaussian profile illumination spot.

Typically, the on/off pixel pattern(s), or patterns of other light modulation effectors, in the selective light modulator(s) is effected via operably connecting the selective light modulator to a controller, such as a PC computer, that individually controls each of the individual light transmission pixels or other light modulation effector. Where the selective light modulator is a DMD or other pixelated device, the controller can control a single mirror as a single pixel or a plurality of mirrors as a single pixel. For example, each individual light transmission pixel can be a grouping of immediately adjacent mirrors, such as set forth in FIGS. 7A and 7B. In particular, FIGS. 7A and 7B schematically depict two different embodiments for illumination comprising the use of adjacent mirrors as a single pixel. In FIG. 7A, a plurality of individual micromirrors of the selective light modulator are turned on as a group. FIG. 7B depicts a similar illumination spot except that different micromirrors (or microshutters or other selected pixel components) have different on/off status and thus provide a Gaussian illumination profile; other illumination profiles are also possible.

In one embodiment for correcting or varying the intensity of the light impinging on the selected target spots of the microarray the light from light source 4 that contacts "off" pixels in the array of the selective light modulator such as digital micromirror device 34 is transmitted to a light detector 37 in FIGS. 1A and 1B. The light detector 37 can receive light directly from the selective light modulator without first going through, or reflecting off, the microarray. The light may or may not go through intervening lenses, filters, etc., between the selective light modulator and the light detector 37. The light detector 37 is typically located at a conjugate image plane of the sample, or in the image plane of the sample itself. When the selective light modulator 34 has all pixels turned "off" all of the light from the light source is transmitted to the detector 37. The detector 37 can then differentiate different levels of intensity within the light emanating from the light source 4, and then to correct for variant intensities via rapid alternating between on and off status to provide a substantially uniform light to microarray 20. This enhances the ability of the system to obtain accurate initial readings from the microarray 20 before the light intensity modulations discussed elsewhere herein. This also permit the microarray reader to have a back up or different approach to measuring the illumination light impinging on the microarray; instead of, or in addition to, figuring the amount of illumination light by measuring the amount of on/off time for the relevant pixels in the selective light modulator, the intensity of the modulated light can be directly measured at the light detector 37, for example by switching the SLM to shine the same portion of light that would go to the microarray to the detector, or by subtracting from the total illumination light intensity the re-directed light that would have gone to the microarray but instead is directed to the detector 37.

In a related embodiment, the light detector and controller can in some embodiments determine the light intensity characteristics of a microarray by detecting the intensity of the light impinging on a detector downstream from the microarray, then modifying the on/off status of the corresponding pixels in the illumination array until a substantially uniform intensity of light is transmitted to the pixels of the detector array, and then determining the light intensity characteristics of the microarray by determining the amount of time that individual pixels in the illumination light array in the selective light modulator are on or off, or otherwise reducing the amount of light transmitted to the microarray.

Figure 6:
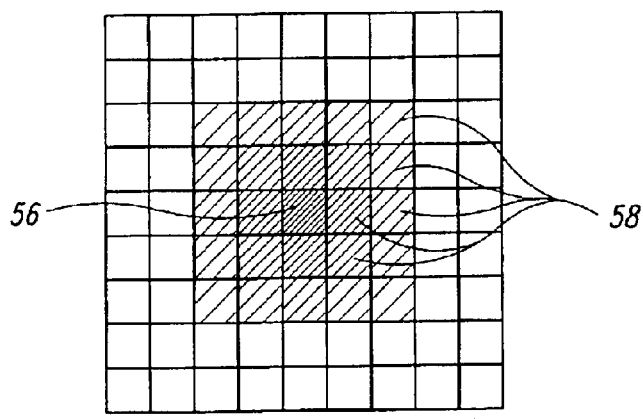
FIG. 6 provides a schematic view of an area of a pixelated light detector for use in the present invention showing an example of the area of the detector illuminated by one of the mirrors of the selective light modulator.

FIG. 6 schematically depicts an embodiment wherein the central detection pixel 56 is more heavily illuminated than adjacent or surrounding pixels 58, but due to the characteristics of the microarray the surrounding pixels are, in fact, illuminated even though only central pixel 56 was directly aligned with the on illumination pixel in the illumination array of the selective light modulator. Thus, in an embodiment that is useful for confocal microscopy and other forms of microarray readers, the microarray reader comprises a controller that contains computer implemented programming that causes the light detector to detect light impinging on a central detection pixel that is aligned with a corresponding individual light transmission pixel of the selective light modulator in the illumination light path that is on and also to detect light impinging on at least one pixel adjacent to the central detection pixel, typically all adjacent pixels. The controller also contains computer-implemented programming that compiles the data provided by the adjacent detection pixel(s) and combines it with the data provided by the central detection pixel to enhance the information provided to and by the microarray reader. For example, such combining of the data can enhance the rejection of the out-of-focus information of the microarray reader when such rejection is compared to the focus that is attained without the data from the adjacent detector(s). Alternatively, the information from the adjacent pixels can provide data about the light scattering and/or absorption or other characteristics of the microarray. Alternatively, if desired, the detector can be set such that the detector and/or controller does not detect information from the central detector pixel that directly corresponds to the on illumination pixel but rather only collects information from the adjacent pixel(s).

Figures 4A, 4B:
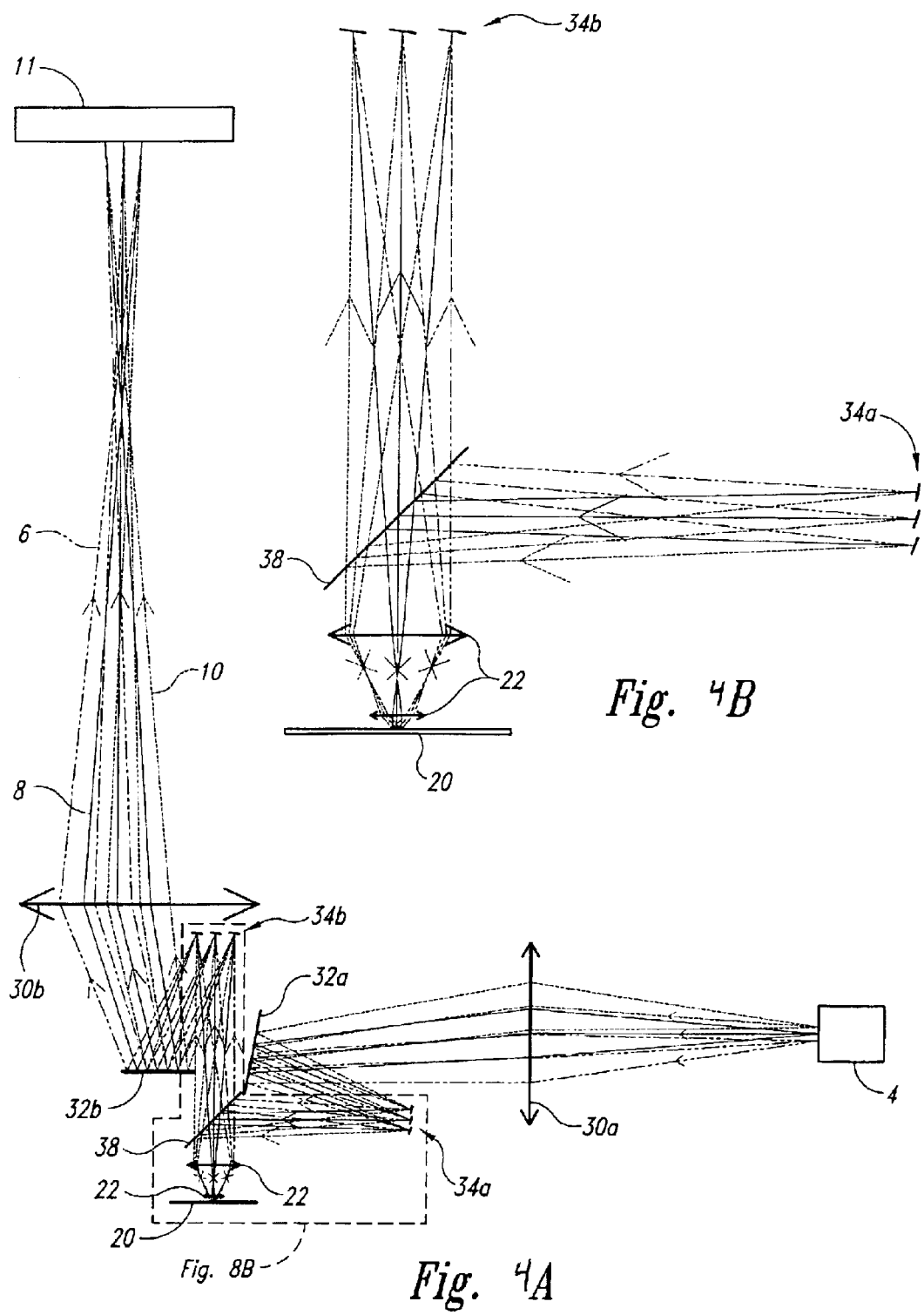
FIGS. 4A and 4B provide a schematic view of a microarray reader according to another embodiment of the present invention that uses two selective light modulators.

FIGS. 4A and 4B depict one example of a microarray reader that is similar to the microarray readers depicted in FIGS. 1 and 3, except that the microarray reader in FIGS. 4A and 4B comprise a first digital micromirror device in a conjugate image plane of the sample that is upstream from the microarray and a second, separate digital micromirror device 34*b* that is located in a conjugate image plane of the sample that is disposed downstream from the microarray. Thus, in FIGS. 4A and 4B, light is emitted by light source 4 through projection lens 30*a* to reflect off simple mirror 32*a* and then selective light modulator 34*a*. Light that is transmitted along the illumination light path by the selective light modulator 34*a* is then reflected off dichroic mirror 38, through objective lenses 22 onto microarray 20, where the light is reflected back through objective lenses 22, then through dichroic mirror 38 and onto downstream selective light modulator 34*b*. Light that is passed by selective light modulator 34*b* continues along the detection path to simple mirror 32*b*, then through projection lens 30*b* to light detector 26. One advantage of the microarray reader depicted in FIGS. 4A and 4B is that, because there are two separate selective light modulators, the two selective light modulators need not have identical on/off status for the light transmission pixels therein. Similar to many other embodiments herein, the embodiment in FIGS. 4A and 4B can be used both with pixelated and non-pixelated detectors such as a photomultiplier tube (PMT), video camera, or other device. In addition, if desired, the detection aperture in the downstream selective light modulator in the detection light path can be dynamically varied in the same manner as described earlier for selective light modulators disposed in the illumination light path.

The modulation of the light striking the light detector 26 can also be effected by modulating the transmission characteristics of the second digital micromirror device 34b that is disposed downstream from the microarray. For example, if the light emanating from the microarray is too bright, then a desired portion of the light can be removed from the detection light path by the second digital micromirror device 34b, and then the on/off status of the second digital micromirror device 34b can be considered in conjunction with the light detected by the detector, to provide the actual spot signal strength, similar to the manner in which the spot signal strength is determined using an upstream selective light modulator.

Figure 5A:
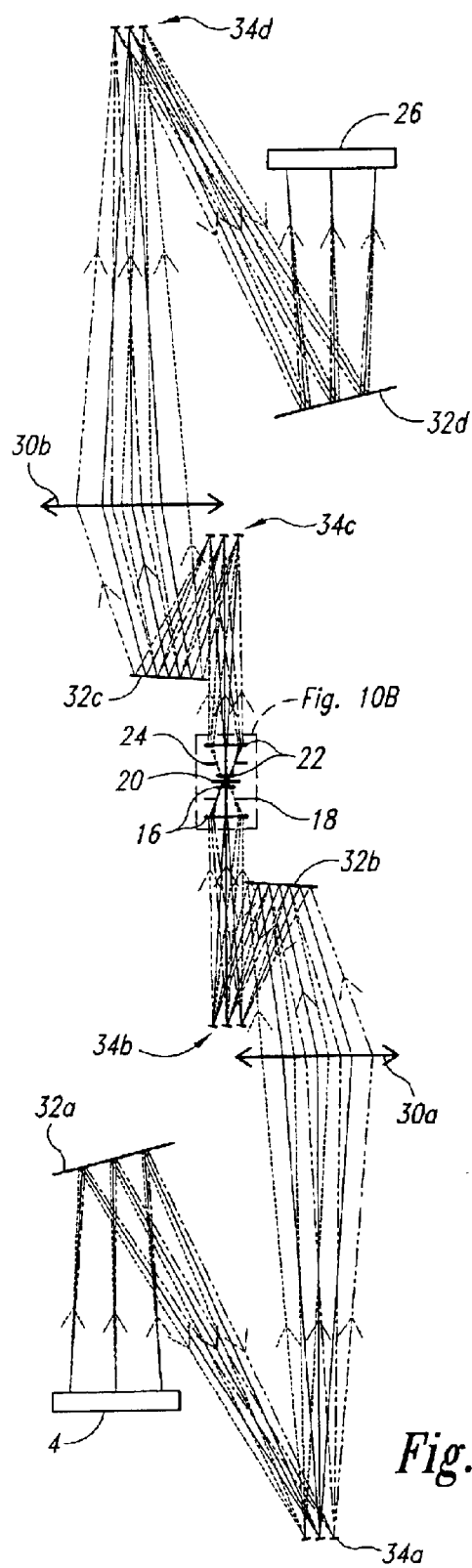
FIGS. 5A and 5B is a schematic view and an expanded schematic view of a microarray reader according to still another embodiment of the invention that comprises four digital micromirror devices to control the light transmission characteristics of the conjugate image plane of the sample and the conjugate image plane of the aperture diaphragm of the objective lens.
Figure 5B:
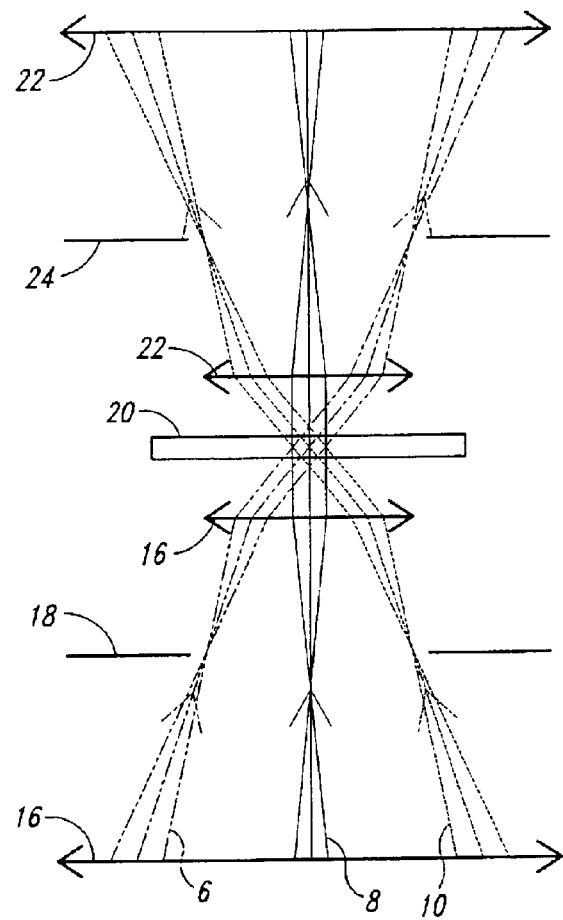

FIGS. 5A and 5B schematically depict one embodiment of a microarray reader suitable for 3-D imaging of the microarray. Briefly, FIGS. 5A and 5B comprise four selective light modulators, two in the illumination light path and two in the detection light path, one in each light path located in the conjugate image plane of the sample and one in each light path located in the conjugate image plane of the aperture diaphragm of the objective lens. Accordingly, in the Figure, light source 4 emits light to simple mirror 32a, which reflects light to a first selective light modulator 34a, which is located in an upstream conjugate image plane of the aperture diaphragm of the objective lens. Selective light modulator 34a transmits a desired portion of light along illumination light path 3 to projection lens 30a, after which it is reflected off simple mirror 32b and transmitted to a second selective light modulator 34b, which selective light modulator is located in an upstream conjugate image plane of the sample. The second selective light modulator 34b then transmits desired light through condensor lenses 16 to microarray 20 where the light is transmitted through the microarray 20, through objective lenses 22 and onto a third selective light modulator 34c, which is located in a downstream conjugate image plane of the sample.

FIGS. 5A and 5B also depict an adjustable iris aperture diaphragm (condenser) 18 that can be disposed between upstream and downstream condenser lenses 16. The light then contacts, or impinges upon, microarray 20 and then proceeds to pass through objective lenses 22, which objective lenses can comprise an aperture diaphragm (objective) 24 space between the objective lenses 22. Diaphragms such as diaphragms 16, 24 can be used with other embodiments of the microarray readers discussed herein if desired. Light that is desired to be transmitted to the light detector 26 is then transmitted by the third selective light modulator 34c to simple mirror 32c where it is reflected through projection lens 30b and onto a fourth selective light modulator 34d, which modulator is located in a downstream conjugate image plane of the aperture diaphragm of the objective lens. The fourth selective light modulator then transmits desired light to simple mirror 32d which reflects the light to light detector 26.

Using the exemplary system of FIGS. 5A and 5B, it is possible to spatially combine various features for selective light modulators located in one or another of the conjugate image planes. For example, combining confocal microscopy with illumination at a variety of angles provides for 3-D confocal transmission and reflectance microscopy. Further, because of the rapid switching time that is possible using the selective light modulators, it is possible to see such 3-D confocal image in real time. Additionally, due to the ability to calculate, and account for, out-of-focus information as discussed herein, such information can be limited and controlled, thereby simplifying the reconstruction task in the making of the 3-D image. Examples of other systems comprising selective light modulators in the conjugate image plane of the aperture diaphragm of the objective lens are discussed in U.S. patent application Ser. No. 09/179,185, filed Oct. 27, 1998.

Configurations such as those depicted in FIGS. 5A and 5B where the microarray reader comprises a selective light modulator in the conjugate image plane of the aperture diaphragm of the objective lens provide additional approaches to modulating the detected signal strength emanating from a given spot(s) on a microarray. Briefly, the selective light modulator in the conjugate image plane of the sample can be used to selectively illuminate or detect a given spot, typically a spot too dim or too bright, then the selective light modulator in the conjugate image plane of the aperture diaphragm of the objective lens can modulate the amount of light to or from the spot by directing undesired light along a different light path, to a beam stop or detector other desired light receptacle.

In alternative embodiments of the invention that account for too dim or too bright spots on microarrays, the dynamic range of a microarray reader can be improved by using differential, known sensitivity settings for different spots. This can be accomplished, for example, by varying the gain settings on a PMT for a scanning spot microarray reader, or by providing different binning options for different image locations on the CCD of a CCD based microarray reader. It is also possible to acquire more than one image with each image having different, known exposure settings. For example, for too dim spots a long exposure time is used and for too bright spots a short exposure time is used. The different images can then be correlated with their respective exposure times and the actual signal strength determined. For a scanning spot microarray reader it is also possible, after the first image has been acquired, to intensity modulate the scanning illumination beam such that bright spots in the images receive a known less amount of light and that the dim spots receive a known larger amount of light.

Another advantage of the present invention is that it permits easily performed time-delayed fluorescence microscopy. This can be accomplished by turning on desired illumination pixels in the selective light modulators in the illumination light path and then turning off corresponding pixels in the selective light modulators (or detector) in the detection light path. After enough time has passed to induce fluorescence in the microarray, which fluorescence can be autofluorescence or fluorescence due to materials, such as dyes, added to the microarray, the selective light modulators in the illumination light path are turned off and short time later the detection pixels of the detector, or the light transmission pixels of selective light modulators disposed in the detection path, are turned on. Examples of suitable timings for such situations are discussed in U.S. patent application Ser. No. 09/179,185, filed Oct. 27, 1998. Such microscopy can be performed both in confocal and wide field modes, or otherwise as desired.

EXAMPLE

A microarray reader similar to the microarray reader depicted in FIGS. 3A and 3B was employed using a DMD (Texas Instruments), conventional microscope optics and illumination design, and an uncooled CCD (KAF-1400 Kodak) with double-correlated 12-bit sampling. Individual DMD mirrors in the illumination path were mapped to CCD camera pixels. A series of gray scale target images of differing intensity were transferred to the DMD to determine the size of the inverse gamma function, which was automatically applied by the DMD formatting electronics to images displayed by the DMD. Using constant illumination, images of a small part of an old and faded (and likely photobleached) spotted microarray were acquired, FIG. 8A. This image was then inverted, the gray levels remapped using an approximate gamma function, the spatial pixel distribution remapped to correspond to the appropriate DMD mirrors, applied to the DMD and a new image, FIG. 8B, was acquired. In this fashion the dim target spots in FIG. 8A received proportionally more illumination than did the bright target spots in FIG. 8A. However, because the light source (an arc lamp) used was not intensity adjustable, the exposure time for FIG. 8B was substantially longer than for FIG. 8A. To calculate the data, the uniform photon count for FIG. 8B was divided by the illumination intensity applied to the DMD before the inverse gamma correction.

As a result of this, in FIG. 8A (non-corrected illumination) the maximum measured density (16 bit image) was 63242. For data measured from FIG. 8B (modulated illumination) the maximum measured intensity was 62976.

In FIG. 8A the measured intensity for area 1 was 1290 with a SD of 155 and a signal-to-noise ratio of 8.2. For data measured from area 1 in FIG. 8B the measured intensity was 1314 with a SD of 143 and a signal-to-noise ratio of 9.1.

In FIG. 8A the measured intensity for the background in area 2 was 380 with a SD of 159 and a signal-to-noise ratio of 2.4. For FIG. 8B the measured intensity for the background in area 2 was 409 with a SD of 99 and a signal-to-noise ratio of 4.1.

FIGS. 9A and 9B, presents histograms of the measurement data from FIGS. 8A and 8B. The first histogram shows the result of 12 bit sampling in a 16 bit image, which can be seen in the discrete nature of the first histogram (since the four most least significant bits are zero), whereas the second histogram represents true 16 bit data. Nevertheless, the noise background of the second histogram is less than the in the in the first histogram, as indicated by the narrower background peak.

Based on these result, noise (uncertainty) in the background of FIG. 8A is 60% greater than that in FIG. 8B, and the respective signal-to-noise ratios of the dim and the bright areas are more similar in FIG. 8B (9.2 for area 1 (bright area) and 4.1 for background) than in FIG. 8A (8.2 for area 1 (bright area) and 2.4 for background).

From the foregoing, it will be appreciated that, although specific embodiments of the invention have been discussed herein for purposes of illustration, various modifications may be made without deviating from the spirit and scope of the invention. Accordingly, the invention includes such modifications as well as all permutations and combinations of the subject matter set forth herein and is not limited except as by the appended claims.

What is claimed is:

1. An automated method of reading a microarray comprising,
   a) providing an initial representation of a microarray comprising a plurality of target spots illuminated by illumination light having a designated intensity;
   b) determining from the initial representation whether at least one of the target spots has an emanating light intensity that is not between selected upper and lower threshold values, and designating such target spot a non-acceptable target spot; and,
   c) modulating the designated intensity of the illumination light via an automated upstream selective light modulator located in an illumination light path substantially at a conjugate image plane of the sample to provide a modulated illumination light and an adjusted target spot that emanates an adjusted light intensity between the selected upper and lower threshold values.

2. The method of claim 1 wherein the method further comprises measuring the amount of modulation of the designated intensity of the illumination light and measuring the adjusted light intensity, then correlating the amount of modulation with the adjusted light intensity to provide a measure of the actual signal strength of the target spot.

3. The method of claim 2 wherein the method further comprises determining an amount of a probe located at the adjusted target spot from the measure of the actual signal strength of the target spot.

4. The method of claim 2 wherein the method is implemented according to a formula:

$$SS(x,y)=K*CCDS(x,y)/II(x,y)$$

where,
   $SS(x,y)$ is the actual signal strength of the target spot,
   $K$ is a constant for the system,
   $(CCDS(x,y))$ is the adjusted light intensity, and
   $(II(x,y))$ is the modulated illumination light.

5. The method of claim 2 wherein the method further comprises detecting a fluorescent target spot.

6. The method of claim 5 wherein the method is implemented according to a formula:

$$SS(x,y)=K*PB(II(x,y),\text{fluoro})*CCDS(x,y)/II(x,y)$$

where,
   $SS(x,y)$ is the actual signal strength of the target spot,
   $K$ is a constant for the system,
   $PB(II(x,y),\text{fluoro})$ is a photobleaching function based on illumination energy/intensity and a fluorophore being excited,
   $(CCDS(x,y))$ is the adjusted light intensity, and
   $(II(x,y))$ is the modulated illumination light.

7. The method of claim 5 wherein the method is implemented according to a formula:

$$SS(x,y)=K*PB(II(x,y),\text{fluoro},x,y)*CCDS(x,y)/II(x,y)$$

where,
   $SS(x,y)$ is the actual signal strength of the target spot,
   $K$ is a constant for the system,
   $PB(II(x,y),\text{fluoro},x,y)$ is a photobleaching function based on illumination energy/intensity, a fluorophore being excited, and a spatial variation term,
   $(CCDS(x,y))$ is the adjusted light intensity, and
   $(II(x,y))$ is the modulated illumination light.

8. The method of claim 2 wherein the modulated illumination light is modulated by changing its illumination intensity.

9. The method of claim 2 wherein the modulated illumination light is modulated by changing its duration of illuminating the target spot.

10. The method of claim 2 wherein the initial representation comprises a precompiled map of expected data for the target spots of the microarray.

11. The method of claim 2 wherein the initial representation comprises an initial image of the plurality of target spots illuminated by the illumination light having the designated intensity and taken by a same microarray reader that implements the determining, modulating, measuring and correlating.

12. The method of claim 11 wherein the initial image is taken substantially immediately before the determining, modulating, measuring and correlating are implemented.

13. The method of claim 2 wherein the method further comprises repeating of the determining, modulating, measuring and correlating using the measure of the actual signal strength as the initial representation.

14. The method of claim 2 wherein the method further comprises selecting a probe such that the modulation is linearly related to the adjusted light intensity.

15. The method of claim 2 wherein the method is implemented using a microarray reader comprising the upstream selective light modulator, and a light detector disposed downstream from the microarray in a detection light path substantially at a conjugate image plane of the sample, wherein the selective light modulator and the light detector are operably connected to at least one controller containing computer-implemented programming that controls transmissive characteristics of the upstream selective light modulator and that compiles the modulated illumination light and the adjusted light intensity, and wherein the controller spatially varies the transmissive characteristics of the selective light modulator to vary the modulated illumination light impinging on the non-acceptable target spots of the microarray such that light emanating from the non-acceptable target spots is between the threshold levels.

16. The method of claim 15 wherein the upstream selective light modulator comprises a digital micromirror device.

17. The method of claim 15 wherein the detector comprises a charge coupled device.

18. An automated method of reading a microarray comprising,
   a) providing an initial representation of a microarray comprising a plurality of target spots illuminated by illumination light having a designated intensity;
   b) determining from the initial representation whether at least one of the target spots has an emanating light intensity that is not between selected upper and lower threshold values, and designating at least one of such target spots a non-acceptable target spot; and,
   c) modulating the emanating light intensity via an automated downstream selective light modulator located in a detection light path substantially at a conjugate image plane of the sample to provide a modulated detection light comprising an adjusted emanating light intensity that is between the selected upper and lower threshold values.

19. The method of claim 18 wherein the method further comprises measuring the amount of modulation of the detection light and measuring the modulated detection light, then correlating the amount of modulation with the modulated detection light to provide a measure of the actual signal strength of the target spot.

20. The method of claim 19 wherein the method further comprises determining an amount of a probe located at the non-acceptable target spot from the measure of the actual signal strength of the target spot.

21. The method of claim 19 wherein the method is implemented according to a formula:

$$SS(x,y)=K*CCDS(x,y)/II(x,y)$$

where,
   $SS(x,y)$ is the actual signal strength of the target spot,
   $K$ is a constant for the system,
   $(CCDS(x,y))$ is the adjusted light intensity, and
   $(II(x,y))$ is the modulated illumination light.

22. The method of claim 19 wherein the method further comprises detecting a fluorescent target spot.

23. The method of claim 22 wherein is implemented according to a formula:

$$SS(x,y)=K*PB(II(x,y),\text{fluoro})*CCDS(x,y)/II(x,y)$$

where,
   $SS(x,y)$ is the actual signal strength of the target spot,
   $K$ is a constant for the system,
   $PB(II(x,y),\text{fluoro})$ is a photobleaching function based on illumination energy/intensity and a fluorophore being excited,
   $(CCDS(x,y))$ is the adjusted light intensity, and
   $(II(x,y))$ is the modulated illumination light.

24. The method of claim 22 wherein the method is implemented according to a formula:

$$SS(x,y)=K*PB(II(x,y),\text{fluoro},x,y)*CCDS(x,y)/II(x,y)$$

where,
   $SS(x,y)$ is the actual signal strength of the target spot,
   $K$ is a constant for the system,
   $PB(II(x,y),\text{fluoro},x,y)$ is a photobleaching function based on illumination energy/intensity, a fluorophore being excited, and a spatial variation term,
   $(CCDS(x,y))$ is the adjusted light intensity, and
   $(II(x,y))$ is the modulated illumination light.

25. The method of claim 19 wherein the initial representation comprises a precompiled map of expected data for the target spots of the microarray.

26. The method of claim 19 wherein the initial representation comprises an initial image of the plurality of target spots illuminated by the illumination light having the designated intensity and taken by a same microarray reader that implements the determining, modulating, measuring and correlating.

27. The method of claim 26 wherein the initial image is taken substantially immediately before the determining, modulating, measuring and correlating are implemented.

28. The method of claim 19 wherein the method further comprises repeating of the determining, modulating, measuring and correlating using the measure of the actual signal strength as the initial representation.

29. The method of claim 19 wherein the method further comprises selecting a probe such that the modulation is linearly related to the adjusted light intensity.

30. The method of claim 19 wherein the method is implemented using a microarray reader comprising the selective light modulator, and a light detector disposed in a detection light path substantially at a conjugate image plane of the sample and downstream from the microarray and the downstream selective light modulator, wherein the selective light modulator and the light detector are operably connected to at least one controller containing computer-implemented programming that controls transmissive characteristics of the downstream selective light modulator and that compiles the modulated detection light and the adjusted light intensity, and wherein the controller selectively varies the transmissive characteristics of the selective light modulator to vary the modulated detection light impinging on the non-acceptable target spots of the microarray such that light received at the detector is between the threshold levels.

31. The method of claim 30 wherein the downstream selective light modulator comprises a digital micromirror device.

32. The method of claim 30 wherein the detector comprises a charge coupled device.

33. A microarray reader comprising an automated upstream selective light modulator located upstream of a microarray in an illumination light path substantially at a conjugate image plane of the sample, and a light detector disposed downstream from the microarray in a detection light path substantially at a conjugate image plane of the sample, wherein the selective light modulator and the light detector are operably connected to at least one controller containing computer-implemented programming that controls transmissive characteristics of the upstream selective light modulator and that compiles an amount of modulated illumination light when the upstream selective light modulator is modulated and an adjusted light intensity emanating from a target spot on a microarray receiving the modulated illumination light, and wherein the controller selectively varies the transmissive characteristics of the selective light modulator to vary the modulated illumination light impinging on at least one non-acceptable target spot of the microarray such that light emanating from the at least one non-acceptable target spot is between selected threshold levels.

34. The microarray reader of claim 33 wherein the controller further comprises computer-implemented programming that controls measuring the amount of modulation of the illumination light and controls measuring the adjusted light intensity, then correlates the amount of modulation with the adjusted light intensity to provide a measure of the actual signal strength of the target spot.

35. The microarray reader of claim 34 wherein the controller further comprises computer-implemented programming that determines an amount of a probe located at the at least one non-acceptable target spot from the measure of the actual signal strength of the target spot.

36. The microarray reader of claim 34 wherein the controller further comprises computer-implemented programming comprising the formula:

$$SS(x,y)=K*CCDS(x,y)/II(x,y)$$

where,
SS(x,y) is the actual signal strength of the target spot,
K is a constant for the system,
(CCDS(x,y)) is the adjusted light intensity, and
(II(x,y)) is the modulated illumination light.

37. The microarray reader of claim 34 wherein the controller further comprises computer-implemented programming comprising the formula:

$$SS(x,y)=K*PB(II(x,y),\text{fluoro})*CCDS(x,y)/II(x,y)$$

where,
SS(x,y) is the actual signal strength of the target spot,
K is a constant for the system,
PB(II(x,y),fluoro) is a photobleaching function based on illumination energy/intensity and a fluorophore being excited,
(CCDS(x,y)) is the adjusted light intensity, and
(II(x,y)) is the modulated illumination light.

38. The microarray reader of claim 34 wherein the controller further comprises computer-implemented programming comprising the formula:

$$SS(x,y)=K*PB(II(x,y),\text{fluoro},x,y)*CCDS(x,y)/II(x,y)$$

where,
SS(x,y) is the actual signal strength of the target spot,
K is a constant for the system,
PB(II(x,y),fluoro,x,y) is a photobleaching function based on illumination energy/intensity, a fluorophore being excited, and a spatial variation term,
(CCDS(x,y)) is the adjusted light intensity, and
(II(x,y)) is the modulated illumination light.

39. The microarray reader of claim 34 wherein the controller further comprises computer-implemented programming comprising a precompiled map of expected data for the target spots of the microarray.

40. The microarray reader of claim 34 wherein the upstream selective light modulator comprises a digital micromirror device.

41. The microarray reader of claim 34 wherein the detector comprises a charge coupled device.

42. A microarray reader comprising an automated downstream selective light modulator located downstream of a microarray in a detection light path substantially at a conjugate image plane of the sample, and a light detector disposed in the detection light path substantially at a conjugate image plane of the sample and downstream from the downstream selective light modulator and the microarray, wherein the downstream selective light modulator and the light detector are operably connected to at least one controller containing computer-implemented programming that controls transmissive characteristics of the downstream selective light modulator and that compiles an amount of modulated detection light when the downstream selective light modulator is modulated and an adjusted light intensity received by the detector, and wherein the controller selectively varies the transmissive characteristics of the downstream selective light modulator to vary the modulated detection light emanating from at least one non-acceptable target spot of the microarray such that light received at the detector from the at least one non-acceptable target spot is between selected threshold levels.

43. The microarray reader of claim 42 wherein the controller further comprises computer-implemented programming that controls measuring the amount of modulation of the detection light and controls measuring the adjusted light intensity, then correlates the amount of modulation with the adjusted light intensity to provide a measure of the actual signal strength of the target spot.

44. The microarray reader of claim 43 wherein the controller further comprises computer-implemented programming that determines an amount of a probe located at the at least one non-acceptable target spot from the measure of the actual signal strength of the target spot.

45. The microarray reader of claim 43 wherein the controller further comprises computer-implemented programming comprising the formula:

$$SS(x,y)=K*CCDS(x,y)/II(x,y)$$

where,
SS(x,y) is the actual signal strength of the target spot,
K is a constant for the system, (CCDS(x,y)) is the adjusted light intensity, and (II(x,y)) is the modulated illumination light.

46. The microarray reader of claim 43 wherein the controller further comprises computer-implemented programming comprising the formula:

$$SS(x,y)=K*PB(II(x,y),\text{fluoro})*CCDS(x,y)/II(x,y)$$

where,

SS(x,y) is the actual signal strength of the target spot,

K is a constant for the system,

PB(II(x,y),fluoro) is a photobleaching function based on illumination energy/intensity and a fluorophore being excited, (CCDS(x,y)) is the adjusted light intensity, and (II(x,y)) is the modulated illumination light.

47. The microarray reader of claim 43 wherein the controller further comprises computer-implemented programming comprising the formula:

$$SS(x,y)=K*PB(II(x,y),\text{fluoro},x,y)*CCDS(x,y)/II(x,y)$$

where,

SS(x,y) is the actual signal strength of the target spot,

K is a constant for the system,

PB(II(x,y),fluoro,x,y) is a photobleaching function based on illumination energy/intensity, a fluorophore being excited, and a spatial variation term, (CCDS(x,y)) is the adjusted light intensity, and (II(x,y)) is the modulated illumination light.

48. The microarray reader of claim 43 wherein the controller further comprises computer-implemented programming comprising a precompiled map of expected data for the target spots of the microarray.

49. The microarray reader of claim 43 wherein the downstream selective light modulator comprises a digital micromirror device.

50. The microarray reader of claim 43 wherein the detector comprises a charge coupled device.

51. An automated method of reading a microarray comprising, a) providing an initial representation of a microarray comprising a plurality of target spots illuminated by illumination light having a designated intensity;

b) determining from the initial representation whether at least one of the target spots has an emanating light intensity that is not between selected upper and lower threshold values, and designating at least one of such target spots as a non-acceptable target spot;

c) selectively illuminating the non-acceptable target spot via selectively transmitting light to the microarray using a first automated upstream selective light modulator located in an illumination light path substantially at a conjugate image plane of the sample; and, d) modulating the designated intensity of the illumination light via a second automated upstream selective light modulator located in the illumination light path substantially at a conjugate image plane of an aperture diaphragm of the objective lens, to provide a modulated illumination light and an adjusted target spot that emanates an adjusted light intensity between the selected upper and lower threshold values.

52. The method of claim 51 wherein the method further comprises measuring the amount of modulation of the designated intensity of the illumination light and measuring the adjusted light intensity, then correlating the amount of modulation with the adjusted light intensity to provide a measure of the actual signal strength of the target spot.

53. The method of claim 52 wherein the method further comprises also modulating the designated intensity of the illumination light via the first automated upstream selective light modulator located in the illumination light path substantially at the conjugate image plane of the sample.

54. The method of claim 52 wherein the method further comprises determining an amount of a probe located at the adjusted target spot from the measure of the actual signal strength of the target spot.

55. An automated method of reading a microarray comprising, a) providing an initial representation of a microarray comprising a plurality of target spots illuminated by illumination light having a designated intensity;

b) determining from the initial representation whether at least one of the target spots has an emanating light intensity that is not between selected upper and lower threshold values, and designating at least one of such target spots as a non-acceptable target spot;

c) selectively detecting light from the non-acceptable target spot via selectively transmitting light from the microarray using a first automated downstream selective light modulator located in a detection light path substantially at a conjugate image plane of the sample; and, d) modulating the emanating light intensity via a second automated downstream selective light modulator located in a detection light path substantially at a conjugate image plane of an aperture diaphragm of the objective lens, to provide a modulated detection light comprising an adjusted emanating light intensity between the selected upper and lower threshold values.

56. The method of claim 55 wherein the method further comprises measuring the amount of modulation of the emanating light intensity and measuring the modulated detection light, them correlating the amount of modulation with the modulation detection light to provide a measure of the actual signal strength of the target spot.

57. The method of claim 56 wherein the method further comprises also modulating the emanating light intensity of the detection light via the first automated downstream selective light modulator located in the detection light path substantially at the conjugate image plane of the sample.

58. The method of claim 56 wherein the method further comprises determining an amount of a probe located at the adjusted target spot from the measure of the actual signal strength of the target spot.

59. A microarray reader comprising a first automated upstream selective light modulator located upstream of a microarray in an illumination light path substantially at a conjugate image plane of the sample, a second automated upstream selective light modulator located upstream of the microarray in the illumination light path substantially at a conjugate image plane of an aperture diaphragm of the objective lens, and a light detector disposed downstream from the microarray in a detection light path substantially at a conjugate image plane of the sample, wherein the first and second selective light modulators and the light detector are operably connected to at least one controller containing computer-implemented programming that controls transmissive characteristics of the first and second upstream selective light modulators and that compiles an amount of modulated illumination light when the second upstream selective light modulator is modulated and an adjusted light intensity emanating from a target spot on a microarray receiving the modulated illumination light, and wherein the controller selectively varies the transmissive characteristics of the second selective light modulator to vary the modulated illumination light impinging on at least one non-acceptable target spot of the microarray such that light emanating from the at least one non-acceptable target spot is between selected threshold levels.

60. The microarray reader of claim 59 wherein the controller further comprises computer-implemented programming that controls measuring the amount of modulation of the illumination light and controls measuring the adjusted light intensity, then correlates the amount of modulation with the adjusted light intensity to provide a measure of the actual signal strength of the target spot.

61. The microarray reader of claim 60 wherein the controller further comprises computer-implemented programming that determines an amount of a probe located at the at least one non-acceptable target spot from the measure of the actual signal strength of the target spot.

62. A microarray reader comprising a first automated downstream selective light modulator located downstream of a microarray in a detection light path substantially at a conjugate image plane of the sample, a second automated downstream selective light modulator located downstream of the microarray in the illumination light path substantially at a conjugate image plane of an aperture diaphragm of the objective lens, and a light detector disposed in a detection light path substantially at a conjugate image plane of the sample and downstream from the first and second downstream selective light modulators and the microarray, wherein the first and second selective light modulators and the light detector are operably connected to at least one controller containing computer-implemented programming that controls transmissive characteristics of the first and second downstream selective light modulator and that compiles an amount of modulated detection light when the second downstream selective light modulator is modulated and an adjusted emanating light intensity received by the detector, and wherein the controller selectively varies the transmissive characteristics of the second downstream selective light modulator to vary the modulated detection light emanating from at least one non-acceptable target spot of the microarray such that light received at the detector from the at least one non-acceptable target spot is between selected threshold levels.

63. The microarray reader of claim 62 wherein the controller further comprises computer-implemented programming that controls measuring the amount of modulation of the detection light and controls measuring the adjusted emanating light intensity, then correlates the amount of modulation with the adjusted emanating light intensity to provide a measure of the actual signal strength of the target spot.

64. The microarray reader of claim 63 wherein the controller further comprises computer-implemented programming that determines an amount of a probe located at the at least one non-acceptable target spot from the measure of the actual signal strength of the target spot.

* * * * *